(12) United States Patent
Levine

(10) Patent No.: US 6,576,435 B1
(45) Date of Patent: Jun. 10, 2003

(54) METHOD FOR PREDICTING REFRACTORY PERIODONTAL DISEASE

(76) Inventor: Martin Levine, 505 Kensington Rd., Norman, OK (US) 73072

(*) Notice: Subject to any disclaimer, the term of this patent is extended or adjusted under 35 U.S.C. 154(b) by 218 days.

(21) Appl. No.: 09/595,004

(22) Filed: Aug. 24, 2000

Related U.S. Application Data

(60) Provisional application No. 60/139,099, filed on Jun. 14, 1999.

(51) Int. Cl.⁷ .................. G01N 33/354; G01N 33/569; G01N 33/53; G01N 33/573
(52) U.S. Cl. .................. 435/7.32; 435/7.1; 435/7.31; 435/7.4; 435/7.2
(58) Field of Search .................. 435/7.1, 7.2, 7.32, 435/7.31, 7.4, 4

(56) References Cited

PUBLICATIONS

Levine et al., Human Serum Precipitins to Human Dental Plaque and Oral Bacteria, Archs oral Biol. vol. 26, pp 117–122, 1981.
Levine et al., Analysis of the Specificity of Natural Human Antibody Reactive to Actinomyces, Molecular Innumology, vol. 23, No. 3, pp 255–261, 1986.
Levine et al., Fast Elisa for Measuring Serum Antibody Responses, Journal of Immunological Methods, 119, pp 211–215, 1989.
Martin Levine, Naturally Occurring Human Serum Precipitins Specific For D–Alanyl Esters of Clycerol Teichoic Acid, Molecular Immunology, vol. 19, No. 1, pp 133–142, 1982.
Levine et al., Human Serum Precipitins to Oral Bacteria Related to Dental Caries, Archs oral Biol., vol. 29, No. 3, pp 191–194, 1984.
Carpino et al., The 9–Fluorenylmethoxycarbonyl Amino– Protecting Group, J. Org. Chem., vol. 37, No. 22, pp 3404–3409, 1972.
James P. Tam, Synthetic Peptide Vaccine Design: Synthesis and Properties of a High–Density Multiple Antigenic Peptide System, Proc.Natl.Acad.Sci.USA, vol. 85, pp 5409–5413, Aug. 1988.
Jeffrey L. Ebersole, Systemic Humoral Immune Responses in Periodontal Disease, Oral Biology and Medicine, pp 283–331, 1990.
Haffajee et al., Attachment Level Changes in Destructive Periodontal Deseases, J Clin Periodontal, 13, pp 461–472, 1986.
Haffajee et al., Clinical, Microbiological and Immunological Features of Subjects With Refractory Periodontal Diseases, J clin Periodontol, 15, pp 390–398, 1988.
Colombo et al., Clinical and Microbiological Features of Refractory Periodontitis Subjects, J Clin Periodontol, 25, pp 169–180, 1998.
Nieminen et al., Prognostic Criteria for the Efficiency of Non–Surgical Periodontal Therapy in Advanced Periodontitis, J Clin Periodontol, 22, pp 153–161, 1995.
Haffajee et al., Clinical and Microbiological Features of Subjects With Adult Periodontitis Who Responded Poorly to Scaling and Root Planing, J Clin Periodontol, 24, pp 767–776, 1997.
Colombo et al., Discrimination of Refractory Periodontitis Subjects Using Clinical and Laboratory Parameters Alone and in Combination, J Clin Periodontal, 26, pp 569–576, 1999.
Socransky et al., Microbial Complexes in Subgingival Plaque, J Clin Periodontol, 25, pp 134–144, 1998.
Holmes et al., Unusual Gram–Negative Bacteria, Including Capnocytophaga, Eikenella, Pasteurella, and Streptobacullus, Bacteriology, 39, pp 499–508.
Sabo et al., Chemical Properties of *Escherichia Coli* Lysine Decarboxylase Including a Segment of its Pyridoxal 5'–Phosphate Binding Site, Biochemistry, vol. 13, No. 4, pp 670–676, 1974.
Phan et al., Spectrophotometric Assay for Lysine Decarboxylase, Analytical Biochemistry, 120, pp 193–197, 1982.
Hogg et al., Occurence of Lipoteichoic Acid in Oral Streptococci, Int. Journal of Systematic Bacteriology, pp 62–66, Jan. 1997.
Warren et al., Biosynthesis of D–Alanyl–Lipoteichoic Acid: Characterization of Ester–Linked D–Alanine in the in Vitro–Synthesized Product, Journal of Bacteriology, pp 293–301, Jul. 1980.

*Primary Examiner*—S. Devi

(57) ABSTRACT

A kit and method of predicting a refractory response in a subject diagnosed as having periodontal disease by measuring serum concentrations of actinomyces antibodies, streptococcal antibodies and lysine decarboxylase antibodies and using the measurement along with other subject information in a set of derived equations.

10 Claims, 3 Drawing Sheets

SEQUENCE LISTING

<160> NUMBER OF SEQ ID NOS: 1

<210> SEQ ID NO 1
<211> LENGTH: 15
<212> TYPE: PRT
<213> ORGANISM: Eikinella corrodens

<400> SEQUENCE: 1

Glu Thr His Ser Thr His Lys Leu Leu Ala Ala Phe Ser Gln Ala
1               5                   10                  15

METHOD FOR PREDICTING REFRACTORY PERIODONTAL DISEASE

CROSS REFERENCE TO RELATED APPLICATIONS

This application claims the benefit of U.S. Provisional Application Serial No. 60/139,099, filed Jun. 14, 1999.

STATEMENT REGARDING FEDERALLY SPONSORED RESEARCH OR DEVELOPMENT

This research was sponsored by NIH-NIDCR Grant DE12556-01. The U.S. Government may have certain rights in this application.

BACKGROUND

Inflammatory adult periodontitis is a major cause of tooth loss in the middle aged and elderly. The gingival sulci of teeth become infected with a complex mixture of bacteria that impair tooth attachment. Mechanical debridement of the teeth-surfaces (scaling and root planing, SRP) is the current basis of prevention. Many patients preserve tooth attachment with regular SRP and home care, but some,.defined as refractory, continue to lose attachment, even after additional therapy, tetracycline and surgery, to supplement SRP efficacy [1,2]. The severity of prior attachment loss increases the likelihood that a patient will be refractory to therapy [3,4], as also does attachment loss in response to initial SRP [5]. The ability to identify refractory subjects at initial examination would provide several functions that are currently lacking in periodontics. It would indicate how patients should be divided to determine differences in host response or bacterial flora a priori, what patients would benefit most from new and experimental therapies and provide an objective criterion for periodontists to warn patients of failure before treatment is begun.

Although patients develop antibody responses to various bacterial antigens, responses to specific bacteria have not been related to disease severity or progression except in a general way. The odds ratio of being refractory increased from 3-fold to 19-fold as the number of bacterial taxa with an antibody concentration >50 µg/ml increased from 3 to 17, out of a total of 85 bacterial taxa examined [6]. Measuring antibody levels to 85 taxa is difficult. A more specific response was the antibody to *Hemophilus aphrophilus* being >50 µg/ml, but the rationale for measuring antibodies to this organism is not clear and a second, more complex laboratory procedure, measuring bacterial DNA to *Streptococcus constellatus*, is also required [6]. The proposed procedure requires only antibody levels, and clinical measurements that all periodontists obtain prior to therapy.

Recent findings suggest that, of 40 bacterial species detected in the sulci pre-therapy, 37% of the variance in attachment level change after initial SRP was predicted by only the amount of *Actinomyces naeslundii* serotype 2 and *Treponema denticola* [5]. *A. naeslundii* extrudes an ornithine-rich antigen that contains an epitope to which an IgG antibody is directed in human serum [7,8]. An antibody response to this Actinomyces antigen is increased in subjects with less plaque, gingivitis and caries [9]. The sulci of refractory patients contain increased numbers of constellatus/anginosus streptococci [2] that possess a streptococcal antigen (e.g., D-alanyl lipoteichoic acid (D-alanyl-LTA)), whereas mitis/oralis streptococci do not possess D-alanyl LTA and increase in healthy sulci [10,11].

*Capnocytophaga sputigena* and *Capnocytophaga ochracea* are indigenous bacteria which, in addition to *Eikenella corrodens*, make lysine decarboxylase. When one or other of these bacteria comprise more than 2.5% of the total bacterial DNA from sulci, the odds ratios that the patient will be refractory is respectively increased 16-fold or 5.8 fold [6]. Lysine decarboxylase activity in healthy or recently cleaned sulci creates inflammation by irritating the dentally attached (DAT) cells of the oral epithelial attachment. Because therapy does not remove indigenous bacteria, increased numbers of bacteria such as *E. corrodens* or Capnocytophaga spp. in the indigenous flora will infect sulci after cleaning and their lysine decarboxylase production will prevent healthy DAT cells from becoming re-established. *E. corrodens* and Capnocytophaga spp. form most of a bacterial cluster group that colonizes healthy and recently cleaned sulci [12].

Subjects with advanced periodontitis (>4 mm attachment loss) are difficult to treat becasue of anatomical difficulties in keeping a low bacterial load [1], whereas subjects with mild disease are easy to treat successfully and inexpensively. The therapeutic response of subjects with moderate periodontitis is unpredictable. At present, the fraction of sulci that bleed when gently probed is the only criterion for whther a patient will be refractory. It is so unsatisfactory that, when periodontists are faced with treatment failure, they do not know whether this was inherent in the patient or the result of an overlooked problem [5]. The object of the present invention is therefore to enable prediction of which patients will be refractory after initial therapy so they can be warned that there is a high risk of treatment failing within two years thereby potentially enabling other treatment options to be identified or at least anticipated.

BRIEF DESCRIPTION OF THE DRAWINGS

FIG. 1 is subdivided into three graphs (A, B, and C) showing standard curves for assaying human serum antibodies.

DESCRIPTION OF THE INVENTION

Figure 1A:
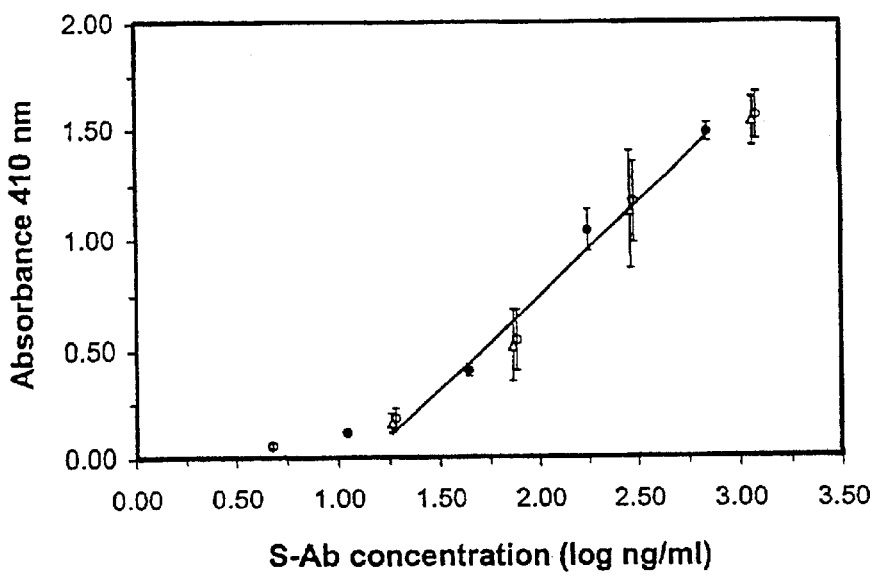
FIG. 1A shows concentrations of streptococcal antibody (S-Ab).

The invention contemplated herein is a method and kit for predicting a refractory response in a subject diagnosed as having periodontal disease. In the method, the subject provides a blood or serum sample. Serum concentrations of actinomyces antibodies, streptococcal antibodies, and lysine decarboxylase antibodies are measured from the blood or serum sample in conjunction with measurements of bleeding on probing (BOP, a standard measure of gingival inflammation) and age. From these antibody concentrations a refractory response score is calculated which is predictive of whether or not the subject is likely to have a refractory response after initial therapy. Antigens which are used to detect the antibodies are in one embodiment, an actinomyces antigen (e.g., an ornithine-rich antigen), a streptococcal antigen, in one is embodiment, D-alanyl glycerol lipoteichoic acid from streptococci, and a lysine decarboxylase, or fragment thereof, obtained from *E. corrodens*, or another sulcal bacterium which produces lysine decarboxylase. The lysine decarboxylase antigen may be SEQ ID NO:1 or a sequence which is at least 80% identical thereto, and in a preferred embodiment is an antigenic portion of the catalytic site of lysine decarboxylase.

In a preferred embodiment, the calculating step comprises determining a first score based on the lysine decarboxylase antibody concentration, determining a second score based on both the actinomyces antibody concentration and the streptococcal antibody concentration, and determining a third score, which is the refractory response score, which is based on the first and second scores. In one embodiment, the first score is also based on a BOP score. In one embodiment, the second score is further based on the deviation of the actinomyces antibody concentration from a predicted actinomyces antibody concentration, and wherein the predicted actinomyces antibody concentration is based on the streptococcal antibody concentration. In one embodiment, the third score is based on the age of the subject.

The present invention further contemplates a kit for use in the method. The kit comprises an actinomyces antigen able to bind to a human serum actinomyces antibody, a streptococcal antigen able to bind to a human serum streptococcal antibody, and a lysine decarboxylase antigen able to a lysine decarboxylase antibody. The kit may further comprise a serum containing a known concentration of human serum streptococcal antibody and a known concentration of lysine decarboxylase antibody.

The present invention contemplates analyzing antibody concentration data in three steps as described in general below.

First, lysine decarboxylase antibody concentration is used with BOP in a logistic regression equation that predicts the probability of a patient losing mean attachment following initial therapy.

The general equation is:

$$pIAL = 1/(1+e^{-(a+b^*BOP+c^*LD-Ab)})$$

The letters 'a', 'b' and 'c' indicate positive or negative constants, '*' is the multiplication symbol. 'BOP' is the percentage of sites bleeding on probing and LD-Ab is the concentration of antibodies to lysine decarboxylase (log ng/ml). Constants 'a', 'b' and 'c' are derived from a group of experimental patients as described elsewhere herein.

The prediction probability of mean attachment loss (pIAL) is determined from the logistic regression equation and has a value between 0.0 and 1.00. A value of 1.00 means that the patient has a 100% probability of attachment loss and a value of 0.00 means zero probability. In practice, the cutoff for predicting probability of attachment loss is the fraction of patients that lose attachment in the experimental population used to derive the equation. Patients for whom pIAL is greater than this fraction are the predicted attachment losers and the remainder are the predicted attachment gainers. Thus, LD-Ab is used to predict whether a patient gains or loses attachment after initial therapy and is expressed as a "first score". The first score is 0 when pIAL is greater than the fraction of attachment losers in the experimental population and a value of 1 if less than this fraction.

Second, the patient's A-Ab (actinomyces) antibody concentrations and S-Ab (streptococcal) antibody concentrations are determined to be "linear" or "non-linear" as determined from a regression equation derived from refractory patients:

$$(A\text{-}Ab)_p = d^*(S\text{-}Ab) + f$$

Constants 'd' and 'f' are positive or negative, '*' is the multiplication symbol and S-Ab is the streptococcal antibody concentration in log ng/ml. From this relationship and the observed S-Ab concentration, a predicted actinomyces concentration $(A\text{-}Ab)_p$ is calculated for each patient. If this estimate is non-linear (more than 'g' above or 'h' below the observed A-Ab concentration where 'g' and 'h' are constants based on the population the equation is derived from, the relationship between these two antibodies, referred to herein as a second score, is designated as non-linear (A/S=1). Otherwise, the second score is designated as linear (A/S=0).

Third, a third score, that is a prediction (p) that a patient is likely to be refractory ($P_{refractory}$) is determined from the logistic regression equation:

$$P_{refractory} = 1/(1+e^{-(q+r^*pIAL+s^*A/S+t^*Age)})$$

'q', 'r', 's' and 't' are negative or positive constants, '*' is the multiplication symbol. 'IAL' is the first score, related to the prediction of attachment loss or gain (0 or 1). A/S is second score, related to the prediction of a linear or non-linear relationship between these antibody responses (0 or 1), and age is given in years. Constant 'q', 'r', 's' and 't' are derived from a group of experimental patients as described elsewherein herein.

The prediction that a patient will be refractory ($P_{refractory}$) (the third score) is determined from this second logistic regression equation. The optimal prediction of refractory response is the fraction of experimental patients refractory to therapy in the population from whom the equation was derived. Patients for whom $P_{refractory}$ is greater than this fraction are predicted to be refractory. The constants for these equations depend on the particular group and number of patients from whom the equations are derived.

EXAMPLES

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus the following examples, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

In a preferred embodiment, the test, as described below, is used for adult periodontitis patients exhibiting a mean attachment loss of 2.0 to 4.0 mm at baseline examination.

The serum concentration of lysine decarboxylase antibody (LD-Ab) detected by the lysine decarboxylase antigen (as described elsewhere herein) is used with BOP to predict value of initial mean attachment loss (pIAL) using the Equation I below, or a similar equation derived from new or additional subjects using the procedures described elsewhere herein. A patient is a predicted initial attachment loser (wherein a first score=0) when the prediction percentage exceeds a threshold such as the fraction of initial attachment losers in the population from which the equation was derived, e.g., >0.35. Otherwise the patient is a predicted initial attachment gainer (wherein a first score=1).

$$pIAL = 1/(1+e^{-(-5.4948+0.0237 \cdot BOP+2.3653 \cdot LD\text{-}Ab)}) \quad (I)$$

Figure 3A:
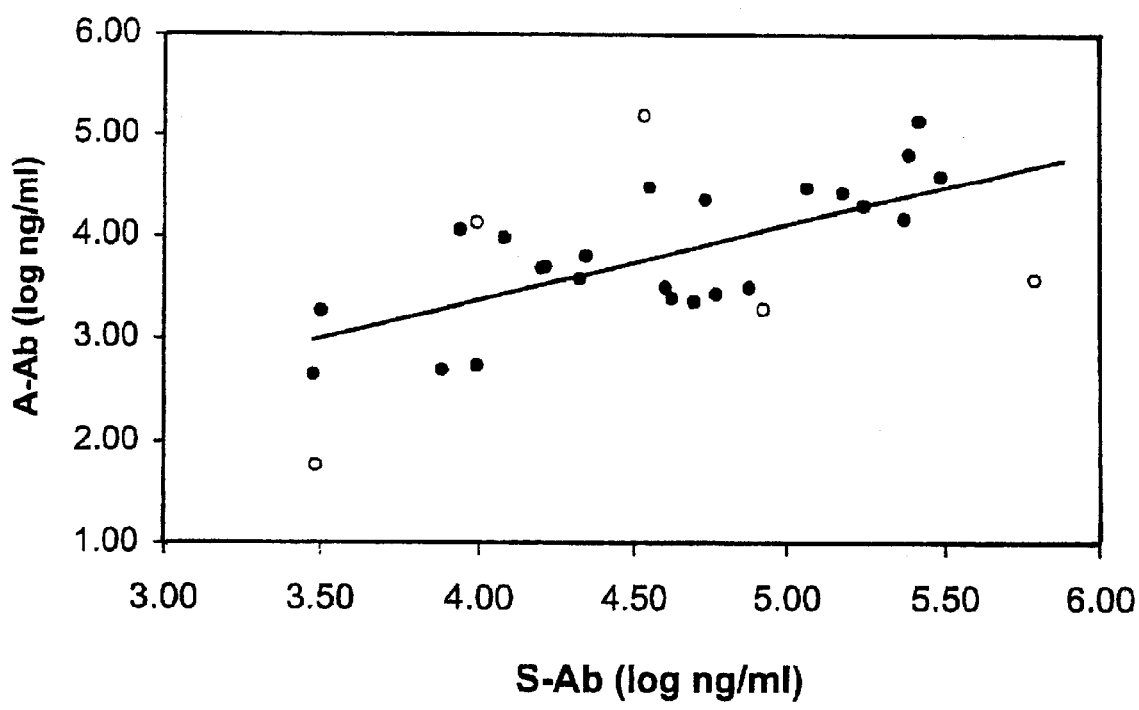
FIG. 3A is a graph showing concentrations of A-Ab and S-Ab in refractory patients and the derived regression curve $(A-Ab)_{pre}=(0.74)$ $(S-Ab)+0.41$. Open circles are designated as "non-linear" while closed circles are designated as "linear."

A predicted concentration of actinomyces antibody $(A\text{-}Ab)_p$ is calculated from S-Ab using a regression equation derived from a population of known refractory patients (e.g., see FIG. 3A).

$$(A\text{-}Ab)_p = 0.74(S\text{-}Ab) + 0.41 \quad (II)$$

Equation II defines a second score known as "A/S". When the actual A-Ab value (log ng/ml) is less than or equal to 0.65 or is greater than or equal to −0.75 the subject is designated as having a "linear" A/S score=0. When the actual A-Ab value is greater than 0.65, or less than −0.75, the subject is designated as having a "non-linear" A/S score=1. The thresholds "0.65" and "−0.75" can be altered based on the population of refractory subjects.

The predicted refractory response "$p_{ref}$" (a third score) is calculated using Equation III below where pIAL is 0 or 1, (A/S) is 0 or 1, and the subject's age is in years as obtained at the baseline exam. A patient is predicted to have a refractory response when the prediction $p_{ref}$ (third score) slightly exceeds a threshold such as the fraction of initial attachment losers in the population from which the equation was derived, e.g., >62% (0.62) for Equation III. In this example, when $p_{ref}$>0.62 the subject is predicted to be refractory. When $p_{ref}\leq 0.62$, the subject is predicted to be non-refractory.

$$p_{ref} = 1/(1+e^{-(-5.0047-2.1285 \cdot pIAL-1.5211 \cdot (A/S)-0.0545 \cdot Age)}) \quad (III)$$

Other versions of I, II, and III could be derived using different populations of subjects.

Antigens

In a preferred embodiment streptococcal antigens and actinomyces antigens are obtained when S. mutans strain GS5 or Actinomyces viscosus ATCC 19246 (respectively) are grown for 4 days in tryptic soy broth and culture filtrates are centrifuged and concentrated 50-fold using a Spiral Regenerated Cellulose column (Millipore Corp., Bedford, Mass.). The streptococcal and actinomyces antigens are detected by electo-immunoassay against an appropriate human serum [8,15]. The streptococcal D-alanyl glycerol LTA antigen is obtained by passing the concentrated culture filtrate over [Sephacryl S200] SEPHACRYL S200 in 0.05 M Na acetate pH 6.0 containing 0.4 M NaCl. Antigen from this column is equilibrated with 0.05 M acetate buffer pH 6 and it binds to AGMP1 a strong anion exchanger (Biorad Laboratories, Hercules Calif.) in this buffer. Increasing the NaCl concentration of the buffer to 1.0 M elutes the antigen [15] and re-equilibration with NaCl-free pH 6 acetate buffer maintains a stable D-alanine ester bond [16]. The lysine decarboxylase antigen, e.g., HKL peptide (or other E. corrodens lysine decarboxylase or a homologous peptide from Capnocytophaga spp.-lysine decarboxylase) is synthesized with the carboxyl end linked to form an 8-branched multiple peptide using the F-moc strategy [17,18].

The amino acid sequence of the lysine decarboxylase encoded by E. corrodens DNA (GenBank Reference Number AAD18126) includes a sequence ETHSTHKLLAAF-SQA (amino acids 359–372) (SEQ ID NO:1) that is 80% or more identical in all sequenced lysine decarboxylases from gram-negative bacteria. This sequence is unique to the attachment site of pyridoxal phosphate, the cofactor and catalytic center of the enzyme [13] and is referred to elsewhere herein as the "HKL" peptide. Measurements of antibodies to the homologous HKL-peptides or other fragments from lysine decarboxylases from C. sputigena, C. ochracea, and C. gingivalis may also be used in the present test. For example the lysine decarboxylase antigens may comprise homologous sequences from Capnocytophaga sputigena and Capnocytophaga ochracea and preferably have at least 80% identity with SEQ ID NO:1.

IgG Antibody Concentrations of Standard Serum

The actinomyces and D-alanyl glycerol LTA IgG antibodies are present at high concentrations in many human sera [23]. Subjects provide a 10 ml vial of blood which is allowed to clot. Each serum is collected and examined by immunoelectrophoresis and one or more of a dozen sera will react strongly [23]. To obtain an antiserum to HKL antigen in Freunds complete or incomplete adjuvant (3 immunizations, 3.0 ml suspension per immunization). The amount of antibody in a standard human serum or in the goat antiserum is measured by immunoprecipitation. Serial 2-fold dilutions of 0.05 ml of purified actinomyces or streptococcal antigen, or of 1.0 mg/ml HKL antigen, are added to 0.3 ml of human standard serum or 0.2 ml of goat antiserum. The mixture is diluted to 1 ml with PBS and incubated overnight at 4° C. The supernatant fractions after centrifugation are discarded and washed 4 times. The sediment is dissolved in 0.1 ml of 0.1 M NaOH and the protein content is measured with the Lowry reagent. The protein concentration precipitated by antigen is low and increases to a maximum as antigen is diluted and then decreases again as antigen is further diluted. The maximal amount of protein precipitated is used to estimate the amount of IgG antibody protein in a fixed volume of serum (0.2 to 0.3 ml).

Optimal Antigen-coating Concentrations

Immunoassay plates are coated with the A or S antigens from 10 liters of culture fluid and in a volume of 10 mls after purification, or HKL antigen dissolved to 1 mg/ml. Actinomyces and Beam Microplate Reader (Dynatech Instruments, Torrance Calif.). The optimal antigen concentration is the greatest dilution of antigen that gives an absorbance reading of not less than 1.7 over one or more of the diluted concentrations. This corresponds to about 3 µg/ml for HKL antigen and about 0.1 mg/ml for the A and S antigens [24].

Measuring JgG Antibody Concentration

Figure 1B:
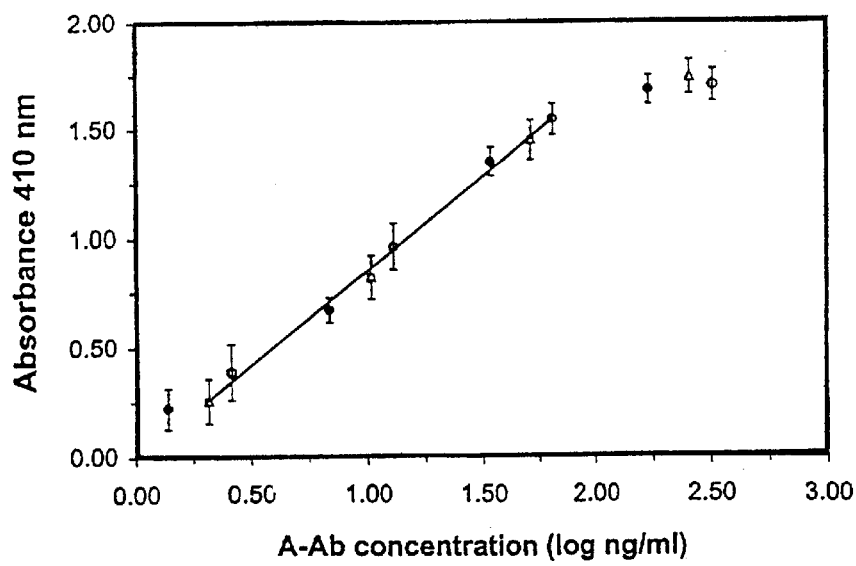
FIG. 1B shows concentrations of actinomyces antibody (A-Ab).
Figure 1C:
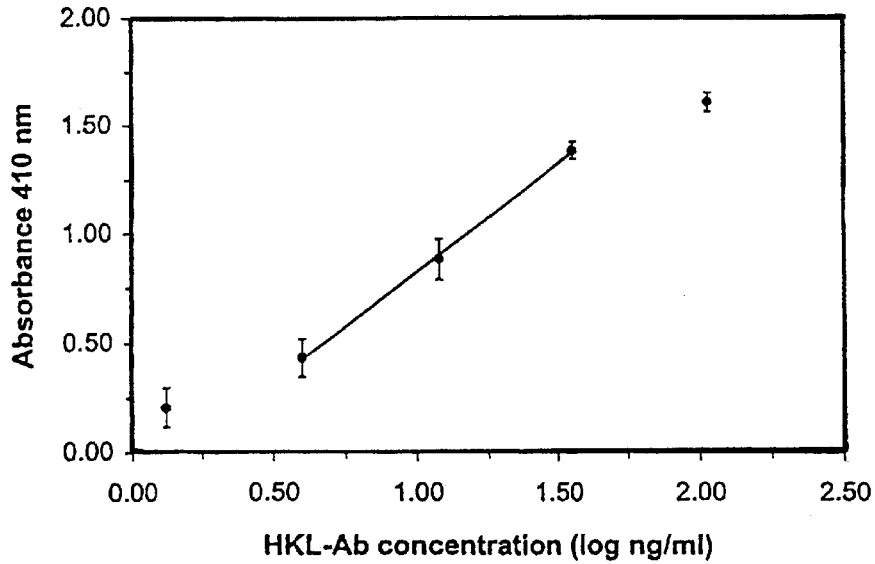
FIG. 1C shows concentrations of lysine decarboxylase antibodies (LD-Ab) S-Ab and A-Ab concentrations were obtained from the amount of protein optimally immunoprecipitated by standard, precipitating human sera. The LD-Ab concentration was estimated by the optimal amount of protein immunoprecipitated by a goat antiserum. For S-Ab (FIG. 1A) and A-Ab (FIG. 1B) absorbance at 410 nm was obtained by enzymoimmunoassay using the appropriate immunoprecipitating human sera and graphed against the-known antibody concentrations. Only the linear portion of each graph is drawn for use in calculating the IgG antibody content of a patient's serum. For LD-Ab (FIG. 1C), the amount of antibody in the control human serum was estimated by comparison with absorbance at 410 nm from the known amount of antibody in the goat anti-serum. Bars indicate standard deviation.

To ensure uniform development of the test sera, dilutions of the appropriate standard serum are added to a column of wells that have been optimally antigen-coated in a plate and developed to the end-point given by these wells in the cross-titration previously. The absorbance at each antibody dilution is graphed against antibody concentration (log ng/ml) and the IgG antibody concentrations of the test sera are calculated from the respective standard curves (FIG. 1). Dilutions of human serum (0.1 ml) in PBS containing 1% albumin and 0.05% [Tween-20] TWEEN-20 (Sigma Chemical Co., St. Louis, Mo.) are added to the coated wells for 1 hour and the wells washed with this buffer without albumin. Anti-human IgG alkaline phosphatase conjugate (0.1 ml of a 1 to 3,000 dilution in PBS containing 0.5% albumin and 0.1% azide) is added for 30 minutes. The wells are washed with the PBS/albumin azide buffer and developed with nitrophenyl phosphate according to the manufacturer's instructions (Sigma Chemical Co., St. Louis, Mo.). HKL antigens are diluted 60-fold with coating buffer 0.5 M carbonate buffer pH 9.6) and S antigen with 0.05 M Na acetate pH 6. Cross-titrations to determine optimal antigen-coating concentrations are made by adding 0.125 ml of the diluted antigen to the first column of wells in an [Immunolon II] IMMUNOLON II Flat-bottom plate (Dynex Corp., Chantilly, Va.) and making serial 5-fold dilutions into each subsequent column of wells. Buffer only is added to the last column (control). The plate is incubated for 2 hours at room temperature and the wells are washed with physiological phosphate buffered saline (PBS). Albumin (0.1 of 0.5% w/v in carbonate buffer, pH 9.6 or phosphate buffer pH 6.0) is added for a further 2 hours (blocking step). The wells are washed again and a standard human serum that precipitates the appropriate antigen during purification (or goat antiserum to HKL antigen) is added to each row of wells (1 to 60 and six serial 5-fold dilutions). Diluent (PBS containing 1% albumin and 0.05% [Tween-20] TWEEN-20; Sigma Chemical Co., St. Louis, Mo.), is added to the last row. After 1 hour, the wells are washed and anti-human or anti-goat IgG conjugated to alkaline phosphatase (Sigma) is added (0.1 ml of a 1 to 3,000 dilution in washing buffer containing 0.5% albumin). After 30 minutes, the wells are washed again and developed by adding nitrophenyl phosphate according to the manufacturer's instructions (Sigma Chemical Co., St. Louis, Mo.). Absorbance is measured with an MR600 [Dynatech] DYNATECH Double-The color intensity from a standard serum ensures uniform antibody measurements from each plate. FIGS. 1A–1C show standard curves of absorbance against antibody concentration for each standard serum.

Analyzing the Data

The probability that mean attachment is lost 3 months after initial therapy, or that the outcome of therapy is unsuccessful (refractory) is obtained by stepwise logistic regression. The equation is: log odds of mean attachment loss=$a+b_1x_1+b_2x_2$ ... where 'a' is a constant, $x_1$, $x_2$, etc. is an independent variable, and $b_1$, $b_2$, etc. is the logarithm of the mean odds ratio for each variable. The independent variables are age, the four baseline measurements indicated in Table 1 and the three obtained antibody concentrations (log ng/ml). Wald's chi-square is used to determine the upper and lower 95% confidence limits of the log odds ratio for each variable. A variable is only retained if this ratio not equal to 1 ($p<0.1$). The significance of the prediction for each patient is determined from a statistic (G) derived from the likelihood ratio test in the presence and absence of each variable. The Goodness-of Fit test ensures that the derived predictions do not significantly differ from what was actually observed [19,20]. The derived equation provides the log odds that therapy will result in periodontal attachment loss 3 months following the initial round of therapy. The anti-log of this value is the probability.

TABLE 1

Effect of initial therapy on severe and minimal periodontitis groups.

| | Pre-therapy | | Post-therapy | | |
|---|---|---|---|---|---|
| | Means | St. Dev. | Means | St. Dev. | 't' test |
| Severe (Bos.) | | | | | |
| Pla | 67.91 | 27.61 | 62.38 | 30.69 | 0.3358 |
| BOP | 43.37 | 36.80 | 36.11 | 33.88 | 0.2977 |
| PD | 3.29 | 0.54 | 3.03 | 0.47 | 0.0088 |
| AL | 3.16 | 1.16 | 3.03 | 1.11 | 0.5321 |
| Minimal (Okla) | | | | | |
| Pla | 66.67 | 17.52 | 51.92 | 22.40 | 0.0109 |
| BOP | 17.63 | 14.87 | 5.45 | 7.89 | 0.0006 |
| PD | 2.345 | 0.384 | 2.034 | 0.298 | 0.0020 |
| AL | 1.154 | 0.500 | 0.763 | 0.547 | 0.0097 |

The equation describing the probability that a patient would lose mean attachment 3 months after initial therapy was obtained after excluding patients with <1.6 mm attachment loss at baseline and/or incomplete clinical measurements. This equation was derived from 51 patients (Table 1) who fit the criteria and 35% of patients initially lost mean attachment in this population. An attachment loser after three months is predicted if the equation exceeds 35%.

The probability that the outcome of a patient's therapy is unsuccessful (refractory) was obtained from 51 patients. Refractory patients were 56% of the population (27/48) and an optimal prediction of being refractory to therapy is when the obtained equation gives a probability of 0.62 or greater.

Antibody, Oral Flora and Response to Therapy

Refractory patients appear to have increased numbers of indigenous lysine decarboxylase-producing bacteria in the oral cavity. Although *E. corrodens* is not increased, other indigenous bacteria making lysine decarboxylase include Capnocytophaga spp. that are increased as noted above [6]. Lysine decarboxylase is not endogenously present in mammals and depleting lysine by this enzyme inhibits mammalian cell growth in vitro because lysine is nutritionally essential. The enzyme from bacteria in healthy or recently cleaned gingival sulci depletes lysine, an essential amino acid, and creates inflammation by preventing the proliferation of dentally attached (DAT) cells that utilize this amino acid in an interstitial fluid transudate at the base of gingival sulci. The disease-associated flora utilizes an inflammatory exudate induced by the inflammation and continues to inhibit DAT cell proliferation by a different mechanism. Therapy removes the disease-associated flora, which is not indigenous. The more bacteria making lysine decarboxylase in the indigenous flora the more difficult it will be to maintain healthy DAT cells after initial SRP. Increased amounts of cadaverine (the product of lysine decarboxylase activity) associate with increased sulcus depth, periodontal pocket formation [14].

Figure 2:
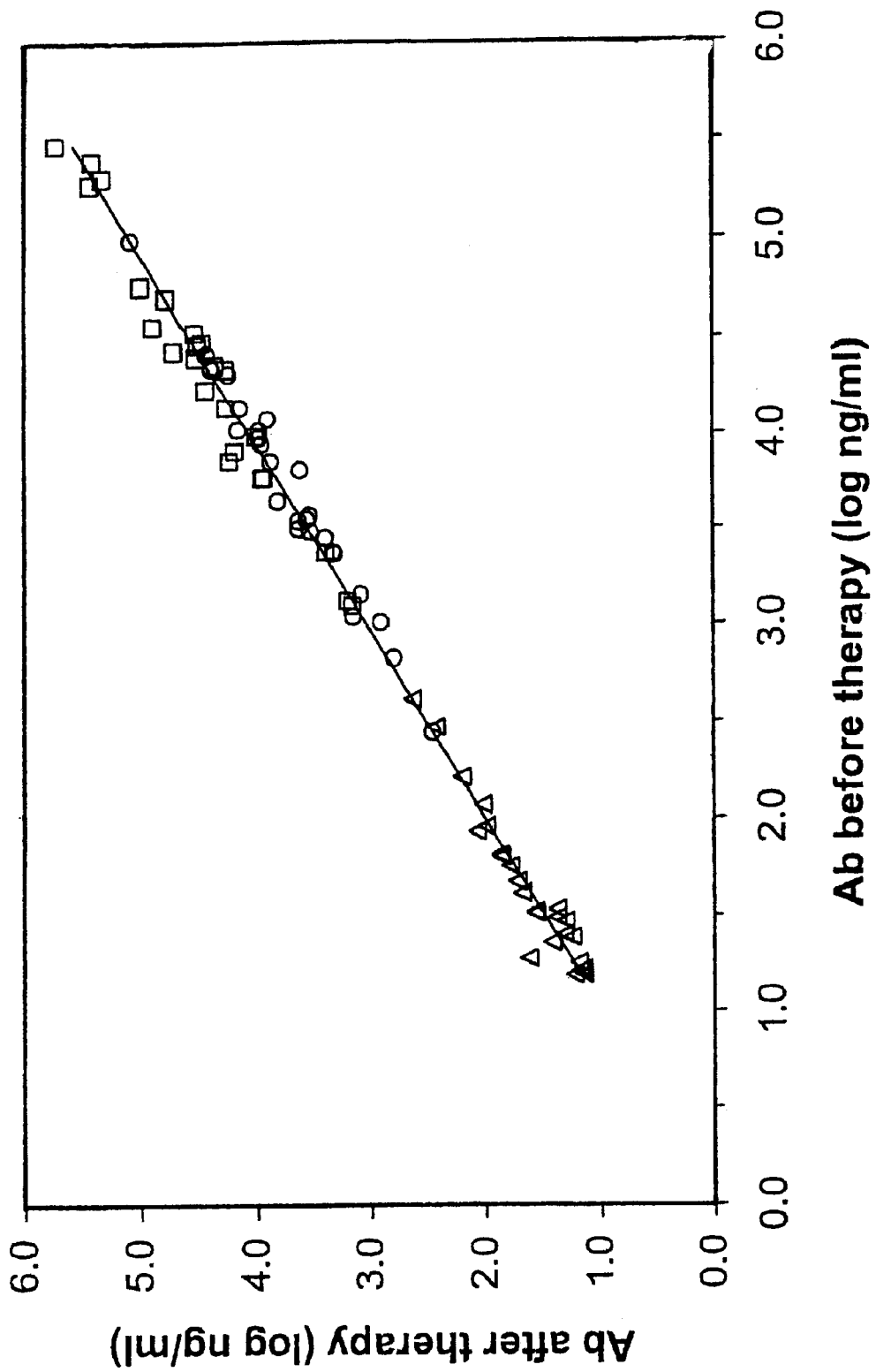
FIG. 2 is a graph showing the respective antibody concentrations in Oklahoma patients. A-Ab (□), S-Ab (○) and LD-Ab (△) concentrations (log ng/ml) were measured at baseline and 6 weeks after SRP therapy was completed.

Table 1 shows baseline measurements and the effect of initial therapy on 52 of 94 Boston patients described by Colombo et al. [6] and on 26 patients from Oklahoma. At baseline, the Boston patients had moderate periodontitis whereas the Oklahoma patients had mild periodontitis. After the initial round of therapy, pocket depth is significantly reduced in the Boston patients, whereas all four measures are significantly reduced in the Oklahoma patients. Thus, the patients with little periodontitis (from Oklahoma) show a marked improvement compared to those with moderate periodontitis (from Boston). FIG. 2 shows that the post-therapy antibody concentrations in the Oklahoma patients (y axis) are essentially unchanged from the concentrations obtained pre-therapy (x axis), and that therapy does not affect antibody response in the most improved patients. The Boston patients that showed less than 1.6 mm mean attachment loss at baseline had mild periodontitis and responded well to therapy like the Oklahoma patients and are therefore excluded from the studies described below. In other words, the diagnostic is only derived from patients who have at least 1.6 mm mean attachment loss at baseline examination.

Table 2 shows the age, clinical and antibody variables in the remaining patients, separated by whether they gained or lost attachment 3 months after initial therapy. Mean attachment decreased by a mean of 0.25 mm in losers and increased by a mean of 0.38 mm in gainers (not shown). Losers and gainers significantly differ by BOP and log LD-Ab content and these two variables alone predict initial mean attachment loss (pIAL) by the Eq. I (p<0.004).

TABLE 2

Age, clinical and antibody findings by gain or loss of attachment following initial therapy in patients with mean baseline attachment loss > 1.6 mm.

| | Measure | | | | |
|---|---|---|---|---|---|
| | 18 Losers | | 33 Gainers | | |
| | Means | S.D. | Means | S.D. | t test, p |
| Age (yrs) | 46.36 | 10.74 | 50.30 | 12.40 | *n.s. |
| Pla (Prevalence, %) | 71.66 | 32.16 | 68.15 | 24.58 | n.s. |
| BOP (Prevalence %) | 61.20 | 39.70 | 32.77 | 29.93 | 0.0094 |
| PD (mm) | 3.38 | 0.36 | 3.28 | 0.61 | n.s. |
| Attachment level (mm) | 3.16 | 0.92 | 3.29 | 1.18 | n.s. |
| Log HKL-Ab conc. (ng/ml) | 1.72 | 0.37 | 1.52 | 0.30 | 0.0335 |
| Log A-Ab conc. (ng/ml) | 3.73 | 0.74 | 3.69 | 0.74 | n.s. |
| Log S-Ab conc. (ng/ml) | 4.61 | 0.63 | 4.51 | 0.64 | n.s. |

*n.s. Not significant (p > 0.2).

As already noted, a patient is a predicted attachment loser after three months (0) if the prediction exceeds 35%. Otherwise a patient is a predicted attachment gainer (1). Table 3 compares the sensitivity and specificity of these measurements. The prediction is significant and has good sensitivity because it correctly assigns most predicted losers as losers, but the specificity is only moderate because a third of gainers are incorrectly predicted to be losers.

TABLE 3

| | Probability of losing attachment 3 months after SRP. | | |
|---|---|---|---|
| Test | Actual Losers | Actual Gainers | Total |
| Predicted losers | 14 | 11 | 25 |
| Predicted gainers | 4 | 22 | 26 |
| Total | 18 | 33 | 51 |

Sensitivity = 77.8%;
Specificity = 66.7%;
Likelihood Ratio = 2.33.
Pos. Assoc. = 56.0%;
Neg. Assoc. = 84.6%
Analysis: $X^2$ = 7.5, O.R. = 7.0 (1.6–33.3), p < 0.01

Figure 3B:
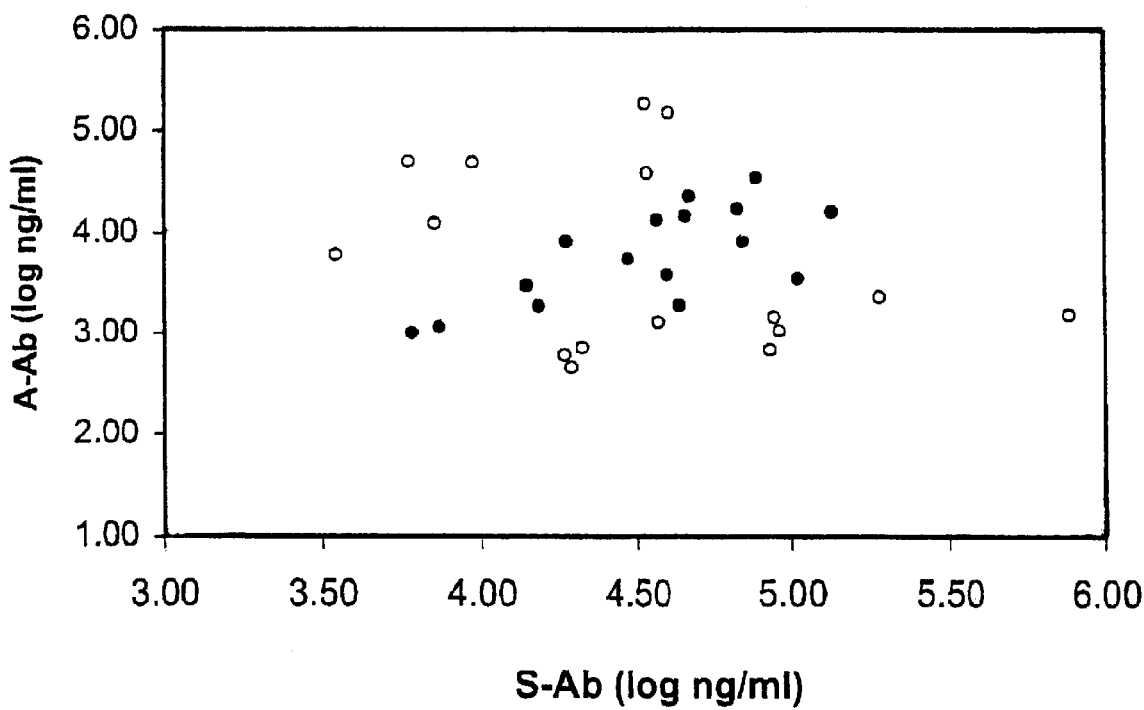
FIG. 3 is a graph showing the A-Ab and S-Ab concentrations in refractory (FIG. 3A) and successfully treated (FIG. 3B) subjects.

The legend to FIG. 3 describes how linear A/S relationship is derived from the A-Ab and S-Ab concentrations in refractory patients. Table 4 shows that the linear A/S relationship significantly predicted a refractory patient with good sensitivity, but poor specificity because a linear A/S relationship occurred in many successfully treated patients. Thus, although LD-Ab content predicts response to initial therapy and a linearly related A/S antibody relationship predicts a refractory outcome, neither prediction is useful alone.

TABLE 4

| | A-Ab/S-Ab linear response and refractory patients | | |
|---|---|---|---|
| Test | Refractory | Successful | Total |
| Linear A-Ab/S-Ab | 24 | 16 | 40 |
| Non-linear | 5 | 16 | 21 |
| Total | 29 | 32 | 61 |

Sensitivity = 82.76%;
Specificity = 50.00%;
Likelihood Ratio = 2.90.
Pos. Assoc. = 60.00%;
Neg. Assoc. = 76.19%
Analysis: $X^2$ = 5.8, O.R. = 4.8 (1.7–33.8), p < 0.02

Following initial therapy, the greater the actinomyces antibody concentration in a patient, the more negative the repopulation of the flora with A. naeslundii, whereas the greater the LD-Ab concentration, the more positive the repopulation of the flora with E. corrodens. The respective antibody contents associate with different and specific bacterial re-colonization patterns following therapy.

Table 5 shows similar findings to Table 2, except that the patients are divided by therapeutic outcome: refractory (0) or successfully treated (1). The probability of refractory response is predicted from a logistic stepwise regression equation. The variables ($x_1$, $x_2$, etc.) were age and the 4 clinical variables and 3 antibody measurements used previously and the percentages of current cigarette/pipe smokers, initial attachment losers, predicted initial attachment losers (pIAL), and those with a linear A/S relationship (A/S). Current smoking and actual initial attachment loss do not associate with refractory response, whereas predicted initial attachment loss and predicted linear A/S relationship significantly associate. From the stepwise regression, predicted initial attachment loss, linear A/S relationship, and age give the best prediction of whether a patient would be refractory to therapy or successfully treated (Eq. III, p<0.001).

TABLE 5

Age, clinical and antibody findings in refractory and successfully treated patients with mean baseline attachment loss > 1.6 mm.

| | Measurement | | | | |
|---|---|---|---|---|---|
| | 27 Refractory | | 21 Successful | | Difference |
| | Means | S.D. | Means | S.D. | t test, p |
| Age | 46.64 | 11.59 | 53.19 | 11.21 | 0.0623 |
| Plaque prevalence | 76.31 | 29.65 | 59.87 | 22.72 | 0.0534 |
| BOP prevalence | 58.04 | 40.17 | 24.51 | 18.80 | 0.0015 |
| Pocket depth (mm) | 3.40 | 0.38 | 3.28 | 0.68 | *n.s. |
| Attachment loss (mm) | 3.32 | 1.06 | 3.31 | 1.08 | n.s. |
| Log HKL-Ab conc. (ng/ml) | 1.63 | 0.33 | 1.53 | 0.35 | n.s. |
| Log A-Ab conc. (ng/ml) | 4.58 | 0.65 | 3.60 | 0.69 | n.s. |
| Log S-Ab conc. (ng/ml) | 3.77 | 0.78 | 4.54 | 0.56 | n.s. |
| % current smokers | 29.60 | | 9.50 | | n.s. |
| % initial attach. losers | 48.15 | — | 19.05 | — | n.s. |

TABLE 5-continued

Age, clinical and antibody findings in refractory and successfully treated patients with mean baseline attachment loss > 1.6 mm.

| | Measurement | | | | |
|---|---|---|---|---|---|
| | 27 Refractory | | 21 Successful | | Difference |
| | Means | S.D. | Means | S.D. | t test, p |
| % pIAL | 66.67 | — | 23.81 | — | §0.0028 |
| % pLA/S | 81.48 | — | 42.86 | — | §0.0135 |

*n.s. Not significant (p > 0.2).
§Chi-square p: For percent attachment loses, $X^2 = 7.041$, and for A/S linear Ab, $X^2 = 6.108$.

Refractory patients were 56% of the population (27/48) and the best prediction of being refractory to therapy was when the equation gave a 0.62 or greater probability. If the patients with moderate attachment loss (mean loss 2–4 mm) are examined separately, the sensitivity is 86.4% and the specificity is 86.7% (Table 6A), whereas the specificity is poor in mild periodontitis patients (62.5%, Table 6B) and the sensitivity is poor in severe periodontitis patients (60.0%, Table 6C). As mild periodontitis patients are nearly all successfully treated and severe periodontitis patients are difficult to treat, this test is most useful for the moderate periodontitis patients, whose response to therapy is the most difficult to predict.

TABLE 6A

Response to therapy determined from age and antibody by initial disease severity.
A. Moderate periodontitis: initial attachment loss 2.0 mm–4.0 mm.

| Prediction | Refractory | Successful | Total |
|---|---|---|---|
| r | 19 | 2 | 21 |
| s | 3 | 13 | 16 |
| Total | 22 | 15 | 37 |

*Includes 4 patients with initial exam measurements only.

TABLE 6B

B. Mild periodontitis: initial attachment loss 1.0–2.0 mm*.

| Prediction | Refractory | Successful | Total |
|---|---|---|---|
| r | 2 | 3 | 5 |
| s | 0 | 5 | 5 |
| Total | 2 | 8 | 10 |

*Includes the 4 successfully treated patients with attachment loss 1.2–1.6 mm not included in deriving the equations and 6 patients with attachment loss 1.6–1.9 mm of whom only 2 provided initial exam measurements.

TABLE 6C

C. Severe periodontitis: initial attachment loss >4.0 mm.

| Prediction | Refractory | Successful | Total |
|---|---|---|---|
| r | 3 | 2 | 5 |
| s | 2 | 5 | 7 |
| Total | 5 | 7 | 12 |

*Includes 1 patient with initial exam measurements only.

The present invention saves both time and money by identifying the patients who may not be able to be treated by conventional periodontal therapy. To have the test done, the periodontist will either draw a blood sample, or have the patient attend a clinic where this can be done. After allowing the blood to clot for 36 h at 4° C., 2 ml of the clear serum is withdrawn and placed in a tube containing 0.1 ml of 1.0% thiomersal solution as a preservative. The sample and a note of the age and percentage of bleeding on probing sites can be mailed or delivered to a central laboratory. The respective antibody concentrations are measured under standardized conditions using the antigen kit described herein and the prediction of a refractory response is determined, for example, by using a software package comprising the equations described herein, or equivalent equations. The result can be communicated to the practitioner who can then design a treatment that would be most cost and time effective for the patient.

Each of the references cited herein is hereby expressly incorporated herein by reference in its entirety. Further the specifications of U.S. Ser. Nos. 08/724,972; 09/113,658; and 09/235,196 issued as U.S. Pat. No. 6,103,220 are also hereby expressly incorporated herein by reference in their entireties.

Changes may be made in the construction and the operation of the various components, elements and assemblies described herein or in the steps or the sequence of steps of the methods described herein without departing from the spirit and scope of the invention as defined in the following claims.

Cited References

1. Haffajee A. D., Socransky S. S., Dzink J. L., Taubman M. A. & Ebersole J. L., Clinical, Microbiological And Immunological Features Of Subjects With Refractory Periodontal Diseases, *J. Clin. Periodontol.*, 15:390–398, 1988.
2. Colombo A. P., Haffajee A. D., Dewhirst F. E., Paster B. J., Smith C. M., Cugini M. A. & Socransky S. S., Clinical And Microbiological Features Of Refractory Periodontitis Subjects, *J. Clin. Periodontol.*, 25:169–180, 1998.
3. Haffajee A. D., Socransky S. S., Smith C. & Dibart S., Relation Of Baseline Microbial Parameters To Future Periodontal Attachment Loss, *J. Clin. Periodontol.*, 18:744–750, 1991.
4. Nieminen A., Siren E., Wolf J. & Asikainien S., Prognostic Criteria For The Efficiency Of Non-Surgical Periodontal Therapy In Advanced Periodontitis, *J. Clin. Periodontol.*, 22: 153–161, 1995.
5. Haffajee A. D., Cugini M. A., Dibart S., Smith C., Kent Jr. R. L. & Socransky S. S., Clinical And Microbiological Features of Subjects With Adult Periodontitis Who Responded Poorly To Scaling And Root Planing, *J. Clin. Periodontol.*, 24:767–776, 1997.
6. Colombo A. P., Haffajee A. D., Smith C. M., Cugini M. A. & Socransky S. S., Discrimination Of Refractory Periodontitis Subjects Using Clinical And Laboratory Parameters Alone And In Combination, *J. Clin. Periodontol.*, 26:569–576, 1999.
7. Levine M. & Bush C. M., Human Serum Precipitins To Human Dental Plaque And Oral Bacteria, *Archs Oral Biol*, 26:117–122, 1981.
8. Levine M. & Movaf agh B. F., Analysis Of The Specificity of Natural Human Antibody Reactive To Actinoinyces, *Mol. Immunol.*, 23:255–261, 1986.
9. Levine M., Brumley R. L., Avery K. T., Owen W. L. & Komori N., Antibody To Actinomyces And Oral Hygiene, *J. Dent. Res.*, 77:776, 1998.

10. Hogg S. D., Whiiey R. A. & De Soet J. J., Occurrence Of Lipoteichoic Acid In Oral Streptococci, *Int. J. Sys. Bacteriol.*, 47:62–66, 1997.
11. Haffajee A. D., Cugini M. A., Dibart S., Smith C., Kent R. L. J. & Socransky S. S., The Effect Of SRP On The Clinical And Microbiological Parameters Of Periodontal Diseases, *J. Clin. Periodontol*, 24:324–334, 1997.
12. Socransky S. S., Haffajee A. D., Cugini M. A., Smith C. & Kent R. L. J., Microbial Complexes In Subgingival Plaque, *J. Clin. Periodontol.*, 25:134–144, 1998.
13. Sabo D. L. & Fischer E. H., Chemical Properties Of *Escherichia coli* Lysine Decarboxylase Including A Segment Of Its Pyridoxal 5'-phosphate Binding Site, *Biochemistry*, 14:670–676, 1974.
14. Walters J. D., Polyamine Analysis Of Human Gingival Crevicular Fluid, *J. Periodontal Res.*, 22:522–523, 1987.
15. Levine M., Naturally Occurring Human Serum Precipitins Specific For D-alanyl Esters Of Glycerol Teichoic Acid, *Mol. Immunol.*, 19:133–142, 1982.
16. Childs W. C III & Neuhaus F. C., Biosynthesis Of D-alanyl-lipoteichoic Acid: Characterization Of Ester-linked D-alanine In The in vitro-synthesized Product, *J. Bacteriol.*, 143:293–301, 1980.
17. Tam J. P., Synthetic Peptide Vaccine Design: Synthesis And Properties-Of A High-Density Phase Multiple Antigenic Peptide System, *Proc. Nat. Acad. Sci. USA*, 85:5409–5413, 1988.
18. Carpino L. A. & Han G. Y., The 9-fluorenylmethoxycarbonyl Amino-Protecting Group, *J. Org. Chem.*, 37:3404–3405, 1972.
19. Hall G. H. & Round A. P., Logistic Regression—Explanation And Use, *J. Royal Coll. Phys.*, 28:242–246, 1994.
20. Hosmer D. W. & Lemeshaw S., *Applied Logistic Regression*, John Wiley & Sons, New York, 1989.
21. Holmes B., Pickett M. J. & Hollis D. G., Unusual Gram-negative Bacteria, Including Capnocytophaga, Eikenella, Pasteurella, And Streptobacillus. In: *Manual Of Clinical Microbiology* (Edited by Murray P. R.) pp. 499–508. ASM Publications, Washington D.C., 1995.
22. Armitage, G., Periodontal Diseases: Diagnosis, *Periodontics*, 1:37–215, 1996.
23. Levine et al., Human Serum Precipitins To Oral Bacteria Related To Dental Caries, *Archs Oral Biol*, 29:191–194, 1984.
24. Levine et al., Fast ELISA For Measuring Serum Antibody Responses, *J. Immunol. Meth.*, 119:211–215, 1989.

What is claimed is:

1. A method for predicting a refractory response in a subject diagnosed as having periodontitis, wherein the refractory response is defined as loss of tooth attachment in the subject after scaling and root planing, surgery, and treatment with tetracycline, the method comprising:

providing a blood or serum sample from a subject diagnosed as having periodontitis;

measuring an actinomyces antibody concentration in the blood or serum sample;

measuring a streptococcal antibody concentration in the blood or serum sample;

measuring a lysine decarboxylase antibody concentration in the blood or serum sample; and calculating a refractory response score predictive of whether the subject is likely to have a refractory response, the refractory response score obtained by combining the lysine decarboxylase antibody concentration, the actinomyces antibody concentration and the streptococcal antibody concentration.

2. The method of claim 1 wherein the calculating step further comprises determining a first score based on the lysine decarboxylase antibody concentration and a second score based on both the actinomyces antibody concentration and the streptococcal antibody concentration, and a third score based on the first score and the second score.

3. The method of claim 2 wherein the first score is further based on a bleeding upon probing score.

4. The method of claim 2 wherein the second score is further based upon the deviation of the actinomyces antibody concentration from a predicted actinomyces antibody concentration.

5. The method of claim 4 wherein the predicted actinomyces antibody concentration is based on the streptococcal antibody concentration.

6. The method of claim 2 wherein the third score is further based on the age of the subject.

7. The method of claim 1 wherein the actinomyces antibody concentration is measured using an actinomyces antigen which is able to bind to human antibodies to actinomyces.

8. The method of claim 1 wherein the streptococcal antibody concentration is measured using a streptococcal antigen which is able to bind to human streptococcal antibodies.

9. The method of claim 1 wherein the lysine decarboxylase antibody concentration is measured using a lysine decarboxylase antigen.

10. The method of claim 9 wherein the lysine decarboxylase antigen is derived from a gram negative bacterial lysine decarboxylase.

* * * * *